(12) United States Patent
Maeda et al.

(10) Patent No.: US 6,613,799 B1
(45) Date of Patent: Sep. 2, 2003

(54) LIPOSOLUBLE PLATINUM (II) COMPLEX AND PREPARATION THEREOF

(75) Inventors: Mitsuaki Maeda, Tokyo (JP); Takuma Sasaki, Tokyo (JP)

(73) Assignee: Sumitomo Pharmaceuticals Company Ltd., Osaka (JP)

( * ) Notice: Subject to any disclaimer, the term of this patent is extended or adjusted under 35 U.S.C. 154(b) by 0 days.

(21) Appl. No.: 06/836,524

(22) Filed: Mar. 5, 1986

(30) Foreign Application Priority Data

Mar. 6, 1985 (JP) .............................. 60-43869

(51) Int. Cl.$^7$ ........................ A01N 55/02; A61K 31/28; C07F 15/00

(52) U.S. Cl. ........................ 514/492; 556/136; 556/137; 554/71; 424/450

(58) Field of Search .................. 556/137, 136; 514/492; 260/414; 424/450; 554/71

(56) References Cited

U.S. PATENT DOCUMENTS

| | | | | | |
|---|---|---|---|---|---|
| 4,203,912 | A | * | 5/1980 | Hydes et al. | ............ 556/137 X |
| 4,225,529 | A | * | 9/1980 | Hydes et al. | ................ 556/137 |
| 4,230,631 | A | * | 10/1980 | Hydes et al. | ................ 556/137 |
| 4,359,425 | A | * | 11/1982 | Totani et al. | ................ 556/137 |
| 4,477,387 | A | * | 10/1984 | Kidani et al. | ............ 556/137 X |
| 4,575,550 | A | * | 3/1986 | Totani | ..................... 556/137 X |
| 5,041,581 | A | | 8/1991 | Khokhar et al. | ............. 556/137 |

FOREIGN PATENT DOCUMENTS

| | | | | |
|---|---|---|---|---|
| EP | 0113508 | | 7/1984 | |
| EP | 0130482 | * | 1/1985 | ................ 556/137 |
| EP | 0136012 | | 4/1985 | |
| FR | 898614 | | 5/1984 | |
| WO | 8702364 | | 4/1987 | ................ 556/137 |

OTHER PUBLICATIONS

"On the preparation, antitumour and cytotoxic evaluation of some new analogues of the cis–dichloro(1,2–diamino–cyclohexane) platinum (II) complex," Craciunescu et al, *Eur. J. Med. Chem.—Chim. Ther.*, vol. 19, No. 4, pp. 353–357 (1984).

CA 105:134160x, "Organoplatinum complexes as antieoplastics," Kihara et al; & JP Kokai 61 37 794 (1986).

"Preparation and antitumor evaluation of water–soluble derivatives of dichloro(1,2–diaminocyclohexane)platinum (II)," Schwartz et al, *Cancer Treatment Report*, vol. 61(8) pp. 1519–1525 (1977).

Kidani et al, Gann, vol. 71 pp. 637–643 (Oct., 1980).

* cited by examiner

*Primary Examiner*—Helen M. S. Sneed
(74) *Attorney, Agent, or Firm*—Miles & Stockbridge; Dennis P. Clarke

(57) ABSTRACT

New derivatives of platinum (II) complex are herein provided, which are liposoluble and applicable as antimicrobial agents and anticancer agents specific to the affected parts of patients and selectively transferred to the parts if they are used in combination with a contrast medium such as lipiodol, the derivatives being represented by the following general formula:

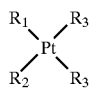

(wherein $R_1$ and $R_2$ may be identical or different with each other and represent an ammine optionally substituted with an organic substituent and they may be bonded together through a bivalent organic group and $R_3$ is a saturated or unsaturated higher fatty acid, these derivatives being prepared by nitrifying a cis-dichloro-di-(substituted or unsubstituted)-ammine platinum (II) and then reacting the resulting aqua type product with a corresponding alkali metal salt of higher fatty acid.

15 Claims, No Drawings

LIPOSOLUBLE PLATINUM (II) COMPLEX AND PREPARATION THEREOF

BACKGROUND OF THE INVENTION

1. Field of the Invention

The present invention relates to a platinum (II) complex. More particularly, the present invention pertains to a platinum (II) complex having excellent antibacterial activity and anticancer activity, in particular, effective to use as a anticancer agent and a process for preparing the same.

2. Description of the Prior Art

Recently, a remarkable development has been achieved in medical and pharmaceutical fields, and as a result, diseases conventionally considered to be incurable and showing a high mortality have been protected, restrained or cured (or recovered) to a substantial degree. Under such circumstances, cancer has drawn a great attention because of its high mortality. However, up to now, there has not yet been proposed an effective solution to reduce the mortality of patients suffering from cancer.

There have been proposed conventional therapeutics for cancer, such as surgical operation inclusive of the operation utilizing laser such as YAG laser in which the affected part of patients is cut off, irradiation (radiotherapy), chemical therapy (chemotherapy) by administrating medicines as well as immunological therapy (immunotherapy) and interferon therapy.

However, the surgical operation and the radiotherapy among others are a kind of locally applied techniques of therapy and are effective means for treating patients only if the disease is in its primitive state or there is no metastasis, while these therapeutics are not effective against the progressive cancer i.e., those accompanying metastasis in the whole body of patients as well as the systematic diseases such as leukemia and malignant lymphoma in which a specific system in the whole body is gradually affected. On the other hand, the chemotherapy is the only effective therapeutics against the latter systematic diseases and some of the cancer may be cured by the chemical therapy. It is also recognized that the chemotherapy is an effective tool for treating patients suffering from cancer, in particular, when it is applied as an additional or auxiliary treatment after the surgical operation or it is applied in combination with the radiotherapy and thus, this is one of the therapeutic technique in which a great future development is expected.

Up to now, various kind of anticancer agents have been developed and proposed and each of them differs in its property and the effectiveness thereof varies depending on the kind of cancer. There may be mentioned such as mitomycin C, adriamycin as the medicine against adenocarcinoma (carcinoma in digestive organs, oophoroma); vincristine, bleomycin against the malignant lymphoma; cytocine arabinoside, L-asparaginase for acute leukemia. On the other hand, a metal complex such as cis-diamminedichloro platinum (II) has recently been proposed and already sold.

The chemotherapy for the cancer is based on the fact that the cancer may be caused by the parasite such as cancer cells in a human body as encountered in the case of bacteria in the general infectious diseases. In other words, the cancer cells are considered to be normal cells which are converted to a variant by some causes and the variant once formed in a body is considered to be the parasite exhibiting autonomous proliferation.

Although, cancer cells as well as normal cells are different in their biological and biochemical properties from each other, the difference is simply a quantitative one, while the qualitative difference between them has not yet been made clear. Therefore, the normal cells may possibly be impaired by the action of chemical agents (medicine) in the chemotherapy and this is revealed as so-called side-effects due to the medicine (such as anticancer agents). Thus, it is quite difficult to restrain only the proliferation of cancer cells or destroy only these cells utilizing such medicines.

BRIEF EXPLANATION OF THE INVENTION

As seen from the above, the development of a new technique for treating cancer is a principal subject to be solved in the medical and pharmaceutic fields and an absolute therapy therefor should be developed. However, it can not be expected to achieve a new drastic development in the therapy such as surgical therapy and the radiotherapy. Thus, it is more preferable or practical to improve chemotherapy or to develop a new medicine since a significant future development may be expected. It is expected, in particular, as the additional or auxiliary treatment means after the surgical operation of the affected part and it may be used in combination with the radiotherapy. Furthermore, the chemotherapy may be an effective tool for treating the progressive cancer as well as the systematic diseases such as malignant lymphoma, leukemia. Thus, there is a great need to develop a new therapeutic technique in medical or pharmaceutical science to remedy the patients suffering from these diseases. It must be said, however, that such agents should fulfill the requirement such that they affect on the cancer cells specifically and preferentially.

The principal object of this invention is to provide a novel platinum (II) complex.

Another object of this invention is to provide a an anticancer composition which affects on cancer cells specifically and preferentially.

A further object of this invention is to provide an anticancer composition having no side-effect.

An other object of this invention is to provide a method for preparing the platinum (II) complex effective as the anticancer active component.

These and other objects of this invention may be accomplished by providing a liposoluble platinum (II) complex represented by the following general formula (I):

(I)

wherein $R_1$ and $R_2$, which may be identical or different, stand for a ligand ammine which may have an organic substituent and may be bonded together through a bivalent organic group and $R_3$ represents a saturated or unsaturated higher fatty acid residue(acyloxy group) and the platinum (II) complex can be prepared according to the following method comprising nitrifying a cis-dichloro-di (substituted or unsubstitutes) ammine platinum (II) complex of the formula (A):

(A)

with a nitrifying agent to form a nitrate of the diaqua form thereof and then reacting the same with a compound of the formula: $R_3$—M (wherein $R_3$ has the same meaning as defined above and M is an alkali metal).

DETAILED EXPLANATION OF THE INVENTION

Conventionally, various kinds of watersoluble platinum (II) complexes have been known and some of them have already been put in practical use. Among the well known examples of such complexes, cisplatin (cis-diamminedichloroplatinum (II)) has been approved and manufactured and sold by BRISTOL-BANYU Pharmaceutical Co., Ltd. and NIPPON KAYAKU Co., Ltd. under the trade name of "Briplatin" and "Randa", respectively.

It is known that the complex is effective to orchidoncus, bladder carcinoma, oophoroma, lung cancer, osteosarcoma, cancer of the esophagus or the like. However, the complex causes a lot of severe side-effects such as diarrhea, celialgia (side-effects in digestive system) and, in particular, this exhibits nephrotoxicity which is known to cause the increase in concentration of blood urea nitrogen (BUN), serum creatinine.

While, carboplatin (cis-diammine-1,1-cyclobutane-dicarboxylate platinum (II); Johnson-Matthey, Inc.), 4'-carboxyphthalato-(1,2-di-aminocyclohexane) platinum (II) (DACCP; Johnson-Matthey, Inc.), spiroplatin (cis-1,1-di-(aminomethyl) cyclohexane platinum (II) sulfate; Organic Chemistry TNO (Utrecht)) or the like have been developed in order to reduce the toxicity, in particular, nephrotoxicity of the cisplatin and to improve the antitumor activity of cis-platinum (II) complex.

These platinum (II) complexes are all water soluble compounds and have water solubility of 17.8 mg/ml (carboplatin), 0.1 mg/ml (DACCP: the solubility in 1.5% $NaHCO_3$ aq. solution being 25 mg/ml) and 1 mg/ml (spiroplatin) respectively. According to these compounds, the nephrotoxicity can somewhat be reduced compared with cisplatin, however, they still exhibit various kinds of side-effects. As stated above these complexes are rather water soluble and they are not considered to be specific and preferential to cancer cells. Therefore, side-effects may possibly be caused due to their rather high water solubility.

Therefore, it is more preferable to obtain a liposoluble platinum (II) complex in order to reduce side-effects of the platinum (II) complex, since the liposolubility may allow the platinum (II) complex to be specific and preferential to cancer cells.

In the platinum (II) complex according to the present invention, the organic substituent in the ligand ammine substituted with organic group(s) and the bivalent organic group through which these two ammine ligands are bonded together may be those used in the conventional anticancer agents consisting of known diammine platinum (II) complexes, as the substituents of the ammine part ($RNH_2$).

In the above liposoluble platinum (II) complex (I), preferred examples are the complexes in which the organic substituent of the ammine ligand ($R_1$ or R 2) is a member selected from the group consisting of alkyl groups having 1 to 5 carbon atoms such as isopropyl group; and cycloalkyl groups having 3 to 7 carbon atoms such as cyclohexyl group. While the preferred example of the bivalent organic group through which two ammine ligands are bonded together is a member selected from the group consisting of cycloalkylene groups; alkylene groups having 2 or 3 carbon atoms, eventually substituted with an alkyl group having 1 to 5 carbon atoms, an alkylene group having 2 to 6 carbon atoms or phenyl group; 1, 2-phenylene group eventually substituted with an alkyl or alkoxyl having 1 to 5 carbon atoms or a halogen atoms. There may be mentioned such as 1,2-cyclohexylene, 2,2-pentamethylene-trimethylene group:

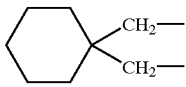

1,1-pentamethylene (ethylene) group:

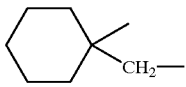

1,2-tetramethylene (trimethylene) group:

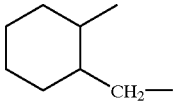

1,2-diphenylethylene, 1,2-phenylene as the most preferred examples of the bivalent organic group.

In the liposoluble platinum (II) complex according to the present invention, isomers, i.e., cis- and trans-form are present when the bivalent organic group is 1,2-cyclohexylene or the like. In this respect, the complex of this invention may be in the form of cis or trans or the mixture thereof.

The substituent $R_3$ in the general formula (I) may be a saturated or unsaturated higher fatty acid and the preferred examples thereof are saturated fatty acids having 10 to 24 carbon atoms such as capric acid, lauric acid, myristic acid, palmitic acid, stearic acid, arachidic acid, behenic acid, lignoceric acid and unsaturated higher fatty acid having 16 to 20 carbon atoms such as oleic acid, linoleic acid.

The liposoluble platinum (II) complex of the present invention, represented by the general formula (I), may easily be prepared according to the following reaction scheme:

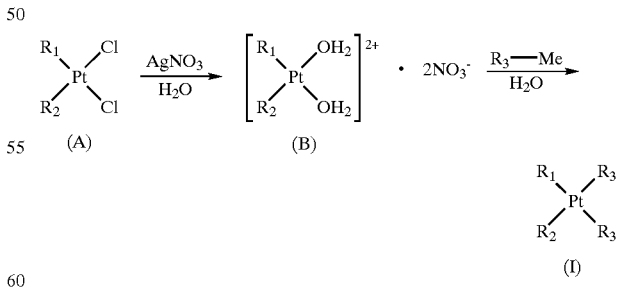

(wherein $R_1$, $R_2$, $R_3$ and M are as defined above)

According to this method, a cis-dichloro-diammine platinum (II) complex (A) is first converted to diaqua form by the action of a nitrifying agent and then the diaqua derivative is subjected to the reaction with a desired alkali metal salt of saturated or unsaturated higher fatty acid to form a saturated or unsaturated higher fatty acid derivative of diammine platinum (II). The nitrification may be carried out using any conventional nitrifying agents such as silver nitrate ($AgNO_3$). Moreover, as the alkali metal M, there may be mentioned, in particular, such as sodium, potassium.

The reaction in which the complex (A) is converted to the diaqua form (B) of the platinum (II) complex is, in general, effected under light shielding condition and the reaction sufficiently proceeds around room temperature. In addition, it is preferred to heat the complex (A) to about 60 to 80° C. prior to the addition of nitrifying agent (such as silver nitrate), in order to easily dissolve the complex (A) into a reaction medium. Although, the reaction time somewhat varies depending on the reaction temperature, the reaction time is, in general, about 3 hours which is sufficient to achieve a good yield.

The reaction (B)–(I) is preferably carried out under light shielding condition as in the reaction of (A)–(B), while the reaction time is around 3 weeks at approximately room temperature.

The cis-dichloro-di-(substituted or unsubstituted)-ammine platinum (II) complexes as the starting material used in the process of this invention are known materials and, for instance, dichlorocyclohexane-1,2-diammine platinum (II) complex is disclosed in the article of T. A. Connors, M. Jones et al., (see, Chem. Biol. Interactions, 1972, 5, 415).

The platinum (II) complex thus obtained according to the process of this invention is liposoluble and thus they may be expected to use as the anticancer agents having a high specificity and selectivity to the cancer cells or antibacterial agents. Moreover, their liposolubility makes it possible to use the complex as a slowly and steadily released and sustained medicine. They become more specific to the affected portion by combining it with a carrier such as any so-called contrast mediums. The preferred is lipiodol which is conventionally used as the contrast medium for hepar, uterus, tuba or the like for the clinical purpose. The lipiodol is iodinated poppy fatty acid ethyl ester and has the $I_2$ content of 38% (w/w), the specific gravity of 1.275 to 1.290, the viscosity of 27 to 43 cSt and the median lethal dose ($LD_{50}$) of 7g/kg when administered intravenously to rabbits. Furthermore, it is also known that the lipiodol is capable of staying stably at the vicinity of the cancer cells for a long period of time. Therefore, if the lipiodol used in combination with the liposoluble platinum (II) complex of this invention, the lipiodol permits the specific sustained action of the latter as the anticancer agent which affects only on the cancer cell and the vicinity thereof.

Thus, the present invention also relates to a composition comprising at least one of the liposoluble platinum (II) complex and at least one of contrast medium. The platinum (II) complex may be administered in the dose of 1 mg/day to 3 g/day for an adult and the composition may be administered intravenously, orally, intrarectally and further it may be injected via a proper artery. They may be used in the form of various pharmaceutical preparations such as tablets, suppositories, injections (for instance, in the form of a solution or a suspension prepared by dissolving or dispersing the active component into a contrast medium such as lipiodol according to any known techniques). It is desirable to use the platinum (II) complex in an amount ranging from 0.1 to 100 mg per 1 to 50 ml of lipiodol. These are used as a solution or a suspension as mentioned above.

As to cyclohexyldiammine derivative of the liposoluble platinum (II) complex as the active component, it is exclusively effective when it is used in combination with lipiodol. Moreover, the use of the contrast medium makes it possible to carry out the diagnosis and the therapy simultaneously and to examine the effectiveness of the treatment while conducting the treatment of patients.

The efficacy of the platinum (II) complex according to the invention, in particular, the anticancer activity is examined according to the following procedures using L 1210 -$CDF_1$ mouse system. First of all, $1\times10^4$ L 1210 leukemia cells were implanted intraperitoneally to the mice and then a solution of the platinum (II) complex in 0.3 ml or 0.2 ml of lipiodol was intraperitoneally injected two times in the mice at 24 hours and 5 days after the implantation of the leukemia cells. The platinum (II) complex was administered in three different doses as shown in the following Table I. In addition, as the controls, mice to which nothing is administered and to which only lipiodol is administered were also examined. Moreover, dispersions of the known compounds such as cis-dichlorodiammine platinum (II) (CDDP) and dichlorocyclohexane-1,2-diammine platinum (II) (DACHP) in lipiodol were administered to mice as the conparative samples and examined their effectiveness. Then, the survival time of each group of mice thus treated was determined and the mean survival time (MST) was estimated on the basis of the observed survival time of each mouse. The effectiveness of the platinum (II) complex was represented by the ratio (T/C) between the mean survival time of the mice to be treated with platinum (II) complex (T) and that of the control group of mice (C) and the ratio (CR) between the number of mice completely cured and total number of mice tested. The results obtained are listed in the following Tables I to III.

TABLE I

| Compound | Dose (mg/kg × 2) | MST | T/C | CR |
|---|---|---|---|---|
| Control | — | 10 | 100 | 0/7 |
| Lipiodol | 385 | 10 | 100 | 0/6 |
| DACHPt(II)- | 833 | 8.0*[1] | Toxic | — |
| $(Myr)_2$ | 167 | — | — | 5/5 |
|  | 33 | 15.0 | 150 | 0/6 |
| DACHPt(II)- | 991 | 17 | 170 | 0/6 |
| $(Pal)_2$ | 198 | 11.5 | 115 | 0/6 |
|  | 40 | 11 | 110 | 0/6 |
| DACHPt(II)- | 1250 | 10.5 | 105 | 0/6 |
| $(Lig)_2$ | 250 | 10 | 100 | 0/6 |
|  | 50 | 10 | 150 | 0/6 |
| DACHPt(II)- | 630 | — | Toxic | 2/7 |
| $(Ole)_2$ | 126 | 17.0 | 170 | 0/6 |
|  | 25 | 13.0 | 130 | 0/5 |

TABLE II

| Compound | Dose (mg/kg × 2) | MST | T/C | CR |
|---|---|---|---|---|
| Control | — | 9.5 | 100 | 0/6 |
| DACHPt(II)- | 1127 | 7.0 | Toxic | — |
| $(Ara)_2$ | 225 | 60 | 600 | 5/5 |
|  | 73 | 20 | 211 | 0/5 |

TABLE III

| Compound | Dose (mg/kg × 2) | MST | T/C | CR |
|---|---|---|---|---|
| Control | — | 8.5 | 100 | 0/6 |
| DACHPt(II)- | 787 | 10.0*[1] | 111 | 0/6 |
| $(Cap)_2$ | 157 | — | Toxic | 2/6 |
|  | 31.5 | 12.0 | 133 | 0/6 |

TABLE III-continued

| Compound | Dose (mg/kg × 2) | MST | T/C | CR |
|---|---|---|---|---|
| DACHPt(II)-(Lau)$_2$ | 855 | 40.0 | 471 | 3/5 |
|  | 171 | 14.0 | 165 | 0/5 |
|  | 57 | 12.0 | 141 | 0/5 |
| DACHPt(II)-(Ste)2 | 1060 | 7.0*$^1$ | Toxic | — |
|  | 212 | — | — | 5/5 |
|  | 71 | 18.0 | 212 | 2/5 |
| DACHPt(II)-(Beh)$_2$ | 1195 | 2.0*$^1$ | Toxic | — |
|  | 239 | — | — | 4/5 |
|  | 80 | 18.0 | 212 | 1/5 |
| CDDP*$^2$ | 58 | 4.0 | Toxic | — |
|  | 11.6 | 15.5 | 182 | 0/5 |
| DACHP*$^2$ | 110 | 4.0 | Toxic | — |
|  | 22 | 7.0 | Toxic | — |

*$^1$In these samples, the platinum (II) complex was administered only one time.
*$^2$Oleic acid moiety was contained in an amount two times larger than the stoichiometric amount based on the molecular weight.
DACH: Cylohexane-1,2-diammine
Cap: Capric acid residue (OCOC$_9$H$_{19}$)

Lau: Lauric acid residue (OCOC$_{11}$H$_{23}$)
Myr: Myristic acid residue (OCOC$_{13}$H$_{27}$)
Pal: Palmitic acid residue (OCOC$_{15}$H$_{31}$)
Ste: Stearic acid residue (OCOC$_{17}$H$_{35}$)
Ara: Arachidic acid residue (OCOC$_{19}$H$_{39}$)
Beh: Behenic acid residue (OCOC$_{21}$H$_{43}$)
Lig: Lignoceric acid residue (OCOC$_{23}$H$_{47}$)
Ole: Oleic acid residue (OCOC$_{17}$H$_{33}$)
CDDP: Cis-dichlorodiammine platinum (II)
DACHP: Dichloro cyclohexane-1,2-diammine platinum (II)

MST and T/C were 8.0 to 10.0 and 100, respectively, in the control group and the group to which only lipiodol was administered and these values were adpcted as the standard. It is the matter of course that CR was 0 in these cases.

As to the groups to which the liposoluble platinum (II) complex according to the present invention is administered, it is observed that mice are sacrificed due to the toxicity of the platinum (II) complex if it was administered in a high dose, however, as to the complex other than the lignoceric acid derivative, excellent results were obtained when the complexes were applied in relatively low dose. In particular, the group of mice to which the lauric acid derivative was administered in the amount of 855 mg/kg shows the CR value of 3/5, the group administered myristic acid derivative in the amount of 167 mg/kg shows that of 5/5; the group to which 212 mg/kg of the stearic acid derivative is administered shows that of 5/5; that of the group to which 225 mg/kg of the arachidic acid derivative is administered is 5/5; that of the group to which 239 mg/kg of the behenic acid derivative is administered is 4/5 and that of the group to which 630 mg/kg of the oleic acid derivative is administered is 2/7.

While, when CDDP or DACHP (known compounds) is applied in a high dose, it was observed that these compounds have a high toxicity and further even if they are administered in a rather low dose, the complete recovery is not observed.

The results, listed in Tables I to III, clearly suggests that there is a close interrelationship between the anticancer activity and the liposolubility of the substituent in the complex.

Moreover, the liposoluble platinum (II) complexes according to the present invention have the sustained, long and steady release property if they are dispersed or dissolved in a contrast medium such as lipiodol, as already mentioned before. Such excellent property thereof can clearly be recognized by observing the results shown in FIG. 1 which were obtained according to the following test:

The liposoluble platinum (II) complex, for example, the cyclohexyldiammine derivative was at first dissolved in lipiodol and then poured into physiological saline solution maintained at 37° C. Under such conditions, the concentration of the platinum (II) complex, in water phase, released from the lipiodol phase was measured while shaking the mixture slowly over a certain period of time. From the results shown in FIG. 1, it is confirmed that the platinum (II) complex is released from the lipiodol phase to the water phase in a sustained slow and steady rate for more than 30 days.

Thus, the platinum (II) complexes excellent in the liposolubility are provided according to the present invention. These complexes are expected to be used, in particular, as the anticancer agents or the antibacterial (antimicrobial) agents. In general, it is required that the cancerocidal, anticarcinoma or antitumorigenic agents as well as other medicines should be specific and preferential to affected portions of patients and that they must not impair the normal cells at all. In this respect, the conventional rather water soluble platinum (II) complexes may possibly impair the normal cells or tissues in patients and has no specificity against the affected parts. While, the platinum (II) complexes according to the present invention exhibit a substantial liposolubility and therefore, if they are used in the form of a solution in a contrast medium having selectivity to a certain portion and staying therein for a long period of time, the required specificity to affected parts and selectivity can substantially be satisfied. Moreover, they are released from the oil phase at sustained, slow and steady rate in the affected portion. Thus, if the complexes according to the present invention are used together with, for instance, lipiodol, they are surely transferred to the affected part (cancer cells) or the vicinity thereof preferentially and stay therein over a long term. As a result, they are gradually released at a sustained and steady rate. This fact permits the simultaneous treatment and diagnosis of patients suffering from malignant cancer, carcinoma or tumor.

Thus, the present invention makes it possible to provide cancerocidal, anticarcinoma or antitumorigenic agents having an extremely effective selectivity to the affected parts and a highly reduced nephrotoxicity compared with those of the conventional water soluble cis-platinum (II) complexes or the like.

The present invention will further be explained in more detail, by the following illustrative examples given below.

EXAMPLE 1

Synthesis of Cyclohexane-1,2-diammine Platinum (II) Dioleate

Starting from cyclohexane-1,2-diammine consisting of about 70% of trans-isomer and about 30% of cis-isomer, dichlorocyclohexane-1,2-diammine platinum (II) complex was prepared according to the method disclosed in Chem. Biol. Interactions, 1972, 5, 415. To 80 ml of distilled water, 570 mg (1.5 mmoles) of the resulting dichlorocyclohexane-1,2-diammine platinum (II) complex was suspended, then the suspension was heated to 70° C. to dissolve most of the complex and after the solution was cooled to room temperature, aqueous solution of silver nitrate (510 mg: 3 mmoles) in 10 ml of water was added to cause reaction between them. The reaction was continued for three hours under stirring and light shielding condition. The resulting reaction product was then filtered off utilizing Celite (manufactured and sold by Johns-Manville) and washed. The filtrate and wash liquid were combined and used in the subsequent reaction without further purification.

To aqueous suspension obtained by dispersing 912 mg (3 mmoles) of sodium oleate into 10 ml of water was added an aqueous solution of the complex in the aqua form obtained before. The reaction was carried out under light shielding condition for 3 weeks, the resulting translucent white precipitates were then recovered by filtration, washed with a small amount of water (10 ml) and dried under reduced pressure to give 1.2 g (yield=92%) of the objective platinum (II) complex which has the following physical and chemical properties:

M. P.: 151~159° C. (dec.); I. R. (cm$^{-1}$); 3180 (b, m), 2845 (s), 1380 (m); 3060 (b, m), 1590 (m), 1060 (w); 2920 (s), 1460 (m), 720 (m);

EXAMPLE 2

The procedures of the Example 1 were repeated except that as the alkali metal salt of higher fatty acid, sodium caprinate, sodium laurate, sodium myristate, sodium palmitate, sodium stearate, sodium arachidate, sodium behenate or sodium lignocerate was used instead of sodium oleate and thus prepared the following platinum (II) complexes:

DACHPt (II) (OCOC$_9$H$_{19}$)$_2$: Yield=61%; M. P. 198~203° C. (dec.); I. R. (cm$^{-1}$): 3170 (b, m), 2840 (m), 1380 (s); 3070 (b, m), 1595 (b, s), 1060 (w); 3020 (s), 1460 (m), 760 (m);

DACHPt (II) (OCOC$_{11}$H$_{23}$)$_2$: Yield=72%; M. P.: 199~206° C. (dec.); I. R. (cm$^{-1}$): 3180 (b, m), 2840 (s), 1380 (s); 3085 (b, m), 1580 (s), 1060 (w); 2910 (s), 1470 (m), DACHPt (II) (OCOC$_{13}$H$_{27}$)$_2$: Yield=92%; M. P.: 178~184 (dec.); I. R. (cm$^{-1}$): 3170 (b, m), 2840 (s), 1380 (s); 3080 (b, m), 1590 (s), 1060 (w); 2910 (s), 1470 (m), 720 (m);

DACHPt (II) (OCOC$_{15}$H$_{31}$)$_2$: Yield=98%; M. P. 188~200° C. (deg.); I. R. (cm$^{-1}$): 3160 (b, m), 2840 (s), 1375 (b, s); 3070 (b, m), 1580 (b, s), 1060 (w); 2910 (s), 1465 (m), 715 (m);

DACHPt (II) (OCOC$_{17}$H$_{35}$)$_2$ Yield=53%; M. P.: 192~202° C. (dec.); I. R. (cm$^{-1}$): 3180 (b, m), 2840 (s), 1470 (m), 720 (m); 3080 (b, m), 1590 (s), 1385 (s); 2910 (s), 1560 (s), 1060 (w);

DACHPt (II) (OCOC$_{19}$H$_{39}$)$_2$: Yield=93%; M. P.: 175~182° C. (dec.); I. R. (cm$^{-1}$) 3170 (b, m), 2845 (s), 1465 (m), 715 (m); 3060 (b, m), 1595 (m), 1385 (m); 2910 (s), 1560 (m), 1060 (w);

DACHPt (II) (OCOC$_{21}$H$_{43}$)$_2$: Yield=88%; M. P.: 200~205° C. (dec.); I. R. (cm$^{-1}$): 3180 (b, m), 2845 (s), 1385 (m); 3060 (b, m), 1560 (m), 1060 (w); 2910 (s), 1470 (m), 720 (m);

DACHPt (II) (OCOC$_{23}$H$_{47}$)$_2$: Yield=94%; M. P.: 163 169° C. (dec.); I. R. (cm$^{-1}$): 3180 (b, m), 2840 (s), 1380 (m); 3060 (b, m), 1590 (s), 1060 (w); 2910 (s), 1460 (m), 720 (m);

EXAMPLE 3

Preparation of Cis-diammine Platinum (II) Dipalmitate

To 30 ml of distilled water was suspended 240 mg (0.8 mmoles) of cis-dichlorodiammine platinum (II) complex, heated at 70° C. to dissolve most of the complex into water and then cooled to room temperature. Thereafter, aqueous solution of silver nitrate (272 mg: 1.6 mmoles) in 10 ml of water was added dropwise to the solution of starting material under stirring. The formation of translucent white precipitates of silver chloride was commenced immediately after the addition of the aqueous solution. The mixed solution was stirred for 3 hours at room temperature under light shielding condition. The resulting precipitates of silver nitrate were filtered off with Celite and washed. The combined filtrate was used in the following step without further treatment.

To aqueous solution of sodium palmitate (400 mg: 1.6 mmoles) in 10 ml of water was added the aqueous solution obtained above and stirred at room temperature for 3 weeks under light shielding condition to complete the reaction therebetween. The translucent white precipitates formed were filtered off, washed with a small amount of ether and dried in vacuo to obtain 0.52 g (yield=88%) of the objective platinum (II) complex. The product has the following properties:

M. P.: 85~87° C.; I. R. (cm$^{-1}$): 3200 (b, m), 1610 (m), 1390 (m), 720 (m); 3090 (b, m), 1590 (m), 1350 (m); 2910 (s), 1550 (m), 1100 (w); 2840 (s), 1465 (m), 870 (b, w);

EXAMPLE 4

The procedures according to the example 3 were repeated except for using sodium myristate, sodium stearate or sodium behenate instead of sodium palmitate and thus the following platinum (II) complexes according to the present invention were prepared. In the following description, the abbreviation "CD" means "cis-diammine"

CDPt (II) (OCOC$_{13}$H$_{27}$)$_2$: Yield=48%; M. P.: 98~102° C. (dec.); 3200 (b, m), 1610 (m), 1380 (m), 720 (w); 3080 (b, m), 1585 (m), 1350 (m); 2910 (s), 1550 (m), 1100 (w); 2840 (s), 1465 (m), 860 (b, w);

CDPt (II) (OCOC$_{17}$H$_{35}$)$_2$ Yield=82%; M. P.: 106~108° C. (dec.); I. R. (cm$^{-1}$): 3200 (b, m), 1610 (m), 1385 (m), 720 (m); 3090 (b, m), 1590 (m), 1350 (m); 2910 (s), 1550 (m), 1100 (w); 2840 (s), 1465 (m), 870 (b, w);

CDPt (II) (OCOC$_{21}$H$_{43}$)$_2$ Yield=91%; M. P.: 95~97° C.; I. R. (cm ): 3200 (b, m), 2840 (s), 1390 (m), 720 (m); 3090 (b, m), 1560 (m), 1105 (w); 2910 (s), 1470 (m), 870 (b, m);

EXAMPLE 5

Preparation of Ethylene-1,2-diammine Platinum (II) Dimyristate 860 mg (2.63 mmoles) of dichloroethylene-1,2-diammine platinum (II) complex was suspended in 140 ml of distilled water and heated to 70° C. to dissolve most of the complex in water and then cooled to room temperature. Thereafter, aqueous solution of silver nitrate (890 mg: 5.26 mmoles) in 20 ml of water was added to the aqueous solution of the complex and stirred for 4 hours under light shielding condition to complete the reaction therebetween. The resulting silver chloride was filtered off by the use of Celite and washed with water. The filtrate and the wash liquid obtained were combined together to use the mixture in the subsequent step without further treatment.

The mixture containing the platinum (II) complex in the aqua form was added to aqueous suspension of sodium myristate (1.32 g: 5.26 mmoles) in 150 ml of distilled water and stirred for 10 days under light shielding condition to cause reaction therebetween. The translucent white precipitates thus produced were recovered by filtration, washed with a small amount of distilled water (20 ml), dried under reduced pressure and thus, 1.58 g (yield=86.4%) of ethylene-1,2-diammine platinum (II) dimyristate having the following physical and chemical properties was obtained:

M. P.: 175~180° C. (dec.); I. R. (cm$^{-1}$): 3180 (b, m), 3100 (b, m), 2920 (s); 2850 (s), 1615 (s), 1590 (s), 1460 (m); 1380 (s), 1310 (w), 1170 (m), 1115 (m); 1055 (m), 870 (w), 720 (w);

The starting material, dichloroethylene-1,2-diammine platinum (II) complex, used in this example was prepared according to the method disclosed in J. Amer. Chem. Soc., 1950, 75, 1840–1841.

What is claimed is:

1. A liposoluble platinum (II) complex represented by the following general formula (I):

(I)

wherein $R_1$ and $R_2$, which may be identical or different, represent a ligand ammine which may have an organic substituent and may be bonded together through a bivalent organic group and $R_3$ represents a saturated higher fatty acid residue having 10 to 24 carbon atoms or unsaturated higher fatty acid residue having 16 to 20 carbon atoms.

2. A liposoluble platinum (II) complex as set forth in claim 1, wherein the organic substituent of the ligand ammine is a member selected from the group consisting of alkyl groups having 1 to 5 carbon atoms and cycloalkyl groups having 3 to 7 carbon atoms.

3. A liposoluble platinum (II) complex as set forth in claim 1, wherein the bivalent organic group is a member selected from the group consisting of cycloalkylene groups; alkylene groups having 2 to 3 carbon atoms, alkylene groups having 2 to 3 carbon atoms, substituted with an alkyl having 1 to 5 carbon atoms, an alkylene having 2 to 6 carbon atoms or phenyl group; 1,2-phenylene group, 1,2-phenylene group substituted with an alkyl or an alkoxyl having 1 to 5 carbon atoms or a halogen atom.

4. A liposoluble platinum (II) complex as set forth in claim 1 wherein $R_1$ and $R_2$ are an unsubstituted ammine.

5. A liposoluble platinum (II) complex as set forth in claim 1 wherein the bivalent organic group, through which these two ammines are bonded together, is 1,2-cyclohexylene group.

6. A liposoluble platinum (II) complex as set forth in claim 1, wherein $R_3$ is oleic acid residue or a saturated fatty acid residue having 10 to 24 carbon atoms.

7. A process for preparing a lipo-soluble platinum (II) complex represented by the following general formula (I):

(I)

wherein $R_1$ and $R_2$, which may be identical or different, stand for a ligand ammine which may have an organic substituent and may be bonded together through a bivalent organic group and $R_3$ represents a saturated higher fatty acid residue having 10 to 24 carbon atoms or unsaturated higher fatty acid residue having 16 to 20 carbon atoms comprising the steps of:

a) nitrifying a cis-dichloro-di (substituted or unsubstituted) ammine platinum (II) compound with a nitrifying agent to form a nitrate of a diaqua form thereof;

b) reacting the resulting diaqua compound with a compound represented by the following general formula:

wherein $R_3$ has the same meaning as defined above and M means an alkali metal.

8. A method according to claim 7 wherein the alkali metal, M, is sodium.

9. A method according to claim 7 wherein the nitrification is carried out using silver nitrate.

10. A pharmaceutical composition comprising 1) an anti-bacterial or anti-cancer effective amount of a liposoluble platinum (II) complex having the following general formula (I):

(I)

wherein $R_1$ and $R_2$, which may be identical or different, stand for a ligand ammine which may have an organic substituent and may be bonded together through a bivalent organic group and $R_3$ represents a saturated higher fatty acid residue having 10 to 24 carbon atoms or an unsaturated higher fatty acid having 16 to 20 carbon atoms, and lipiodol and 2) a pharmaceutically acceptable carrier therefor.

11. The liposoluble platinum (II) complex as set forth in claim 1, wherein the bivalent organic group, through which these two ammines are bonded together, is 1,2-cyclohexylene, and $R_3$ is oleic acid residue or a saturated fatty acid residue having 10 to 24 carbon atoms.

12. The liposoluble platinum (II) complex as set forth in claim 11, wherein $R_3$ is Myristic acid residue.

13. A liposoluble platinum (II) complex represented by the following formula (I):

(I)

wherein $R_1$ and $R_2$, which may be identical or different, stand for a ligand ammine which may have an organic substituent, said organic substituent being a member selected from the group consisting of alkyl groups having 1 to 5 carbon atoms and cycloalkyl groups having 3 to 7 carbon atoms, and may be bonded together through a bivalent organic group, said organic bivalent group being a member selected from the group consisting of cycloalkylene groups; alkylene groups having 2 to 3 carbon atoms, eventually substituted with an alkyl having 1 to 5 carbon atoms, an alkylene having 2 to 6 carbon atoms or a phenyl group; 1,2-phenylene group, eventually substituted with an alkyl or an alkoxyl having 1 to 5 carbon atoms or a halogen atom, and $R_3$ represents a saturated higher fatty acid residue having 10 to 24 carbon atoms or unsaturated higher fatty acid residue having 16 to 20 carbon atoms.

14. A method of treating an animal afflicted with tumor cells sensitive to a platinum (II) 4-coordinate complex comprising administering to said animal a pharmaceutically effective amount of the complex of claim 1 or the composition of claim 10.

15. A composition according to claim 10 in kit form wherein said platinum (II) complex and said lipiodol are separately packaged.

* * * * *